US00PP33453P2

(12) United States Plant Patent
Roe

(10) Patent No.: US PP33,453 P2
(45) Date of Patent: Sep. 7, 2021

(54) CLEYERA PLANT NAMED 'WMN-01'

(50) Latin Name: *Ternstroemia gymnanthera*
Varietal Denomination: WMN-01

(71) Applicant: James Michael Roe, Covington, LA (US)

(72) Inventor: James Michael Roe, Covington, LA (US)

(73) Assignee: WINDMILL NURSERY LLC, Franklinton, LA (US)

( * ) Notice: Subject to any disclaimer, the term of this patent is extended or adjusted under 35 U.S.C. 154(b) by 0 days.

(21) Appl. No.: 17/060,031

(22) Filed: Sep. 30, 2020

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. Anne Whealy

(57) ABSTRACT

A new and distinct cultivar of *Cleyera* plant named 'WMN-01', characterized by its uniform and outwardly branching plant habit; vigorous growth habit; freely branching habit, dense and bushy appearance; glossy dark green, greyed green and light greenish yellow variegated leaves that are lightly blushed with purplish red under cool season conditions; and good garden performance, tolerant to full sunlight to shade conditions.

2 Drawing Sheets

Figure 1:
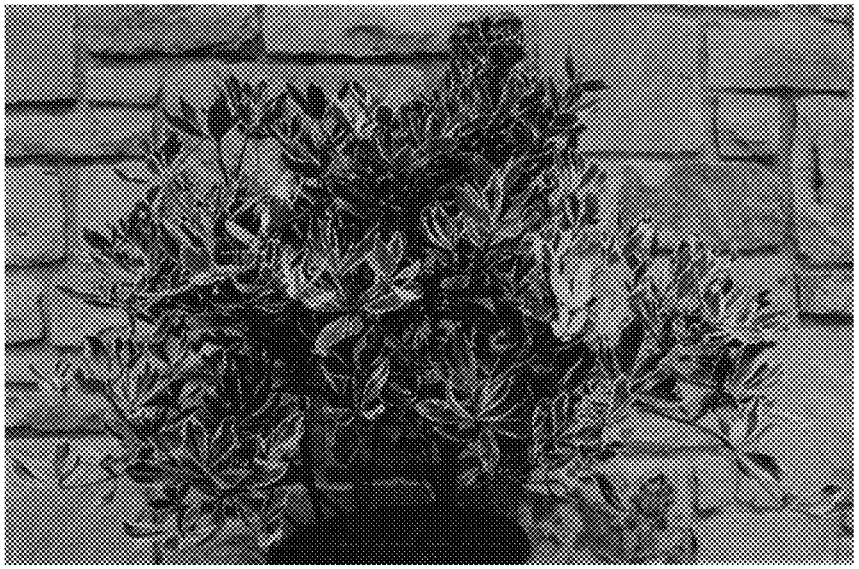

Botanical designation: *Ternstroemia gymnanthera.*
Cultivar denomination: 'WMN-01'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present Invention relates to a new and distinct cultivar of *Cleyera* plant, botanically known as *Ternstroemia gymnanthera*, and hereinafter referred to by the name 'WMN-01'.

The new *Cleyera* plant is a naturally-occurring branch mutation of an unidentified proprietary seedling selection of *Ternstroemia gymnanthera*, not patented. The new *Cleyera* plant was discovered and selected by the Inventor on a single plant within a population of plants of the unidentified seedling selection in an outdoor nursery in Franklinton, La. on May 1, 2009.

Asexual reproduction of the new *Cleyera* plant by vegetative cuttings in a controlled environment in Franklinton, La. since May 3, 2009 shown that the unique features of this new *Cleyera* plant are stable and reproduced true to type in successive generations.

SUMMARY OF THE INVENTION

Plants of the new *Cleyera* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'WMN-01'. These characteristics in combination distinguish 'WMN-01' as a new and distinct cultivar of *Cleyera:*

1. Uniform and outwardly branching plant habit.
2. Vigorous growth habit.
3. Freely branching habit, dense and bushy appearance.
4. Glossy dark green, greyed green and light greenish yellow variegated leaves that are lightly blushed with purplish red under cool season conditions.
5. Good garden performance, tolerant to full sunlight to shade conditions.

Plants of the new *Cleyera* differ primarily from plants of the mutation parent selection in the following characteristics:

1. Plants of the new *Cleyera* have variegated leaves whereas plants of the mutation parent selection have green-colored leaves without any variegation.
2. Under cool season conditions, leaves of plants of the new *Cleyera* are lightly blushed with purplish red whereas leaves of plants of the mutation parent selection maintain their green coloration under cool season conditions.

Plants of the new *Cleyera* can be compared to the plants of *Ternstroemia gymnanthera* 'Broody', disclosed in U.S. Plant Pat. No. 30,450. In side-by-side comparisons plants of the new *Cleyera* differ from plants of 'Broody' in the following characteristics:

1. Plants of the new *Cleyera* are more uniform than plants of 'Broody'.
2. Plants of the new *Cleyera* are more vigorous and denser than plants of 'Broody'.
3. Leaves of plants of the new *Cleyera* are dark green, greyed green and light greenish yellow variegated whereas leaves of plants of 'Broody' are light greenish yellow and yellow green variegated.

BRIEF DESCRIPTION OF THE PHOTOGRAPHS

The accompanying colored photographs illustrate the overall appearance of the new *Cleyera* plant showing the colors as true as it is reasonably possible to obtain in colored reproductions of this type. Colors in the photographs may differ slightly from the color values cited in the detailed botanical description, which accurately describe the colors of the new *Cleyera* plant.

The photograph on the first sheet (FIG. 1) is a side perspective view of a typical plant of 'WMN-01' grown in a container.

Figure 2:
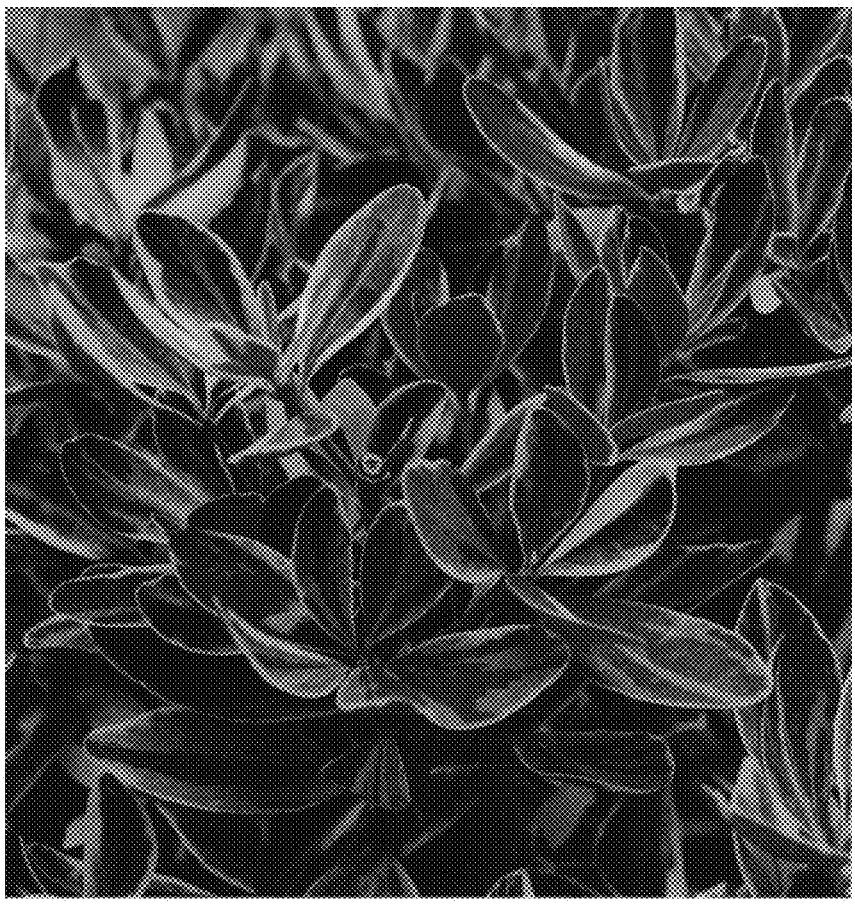

The photograph on the second sheet (FIG. 2) is a close-up view of a typical plant of 'WMN-01'.

DETAILED BOTANICAL DESCRIPTION

The aforementioned photographs and following observations and measurements describe plants grown in Franklinton, La. and Fort Worth, Tex. in 7-gallon containers in an outdoor nursery during the spring and summer and under cultural practices typical of commercial *Cleyera* production. During the production of the plants, day temperatures ranged from 18° C. to 38° C. and night temperatures ranged from 15° C. to 21° C. Plants were 30 months old when the photographs and description were taken. In the following description, color references are made to The Royal Horticultural Society Colour Chart, 2015 Edition, except where general terms of ordinary dictionary significance are used.

Botanical classification: *Ternstroemia gymnanthera* 'WMN-01'.

Parentage: Naturally-occurring branch mutation of an unidentified proprietary seedling selection of *Ternstroemia gymnanthera*, not patented.

Propagation:

*Type*.—By vegetative cuttings.

*Time to initiate roots, summer*.—About 45 days at temperatures about 29° C.

*Time to initiate roots, winter*.—About 70 days at temperatures about 21° C.

*Time to produce a rooted young plant, summer*.—About 90 days at temperatures about 29° C.

*Time to produce a rooted young plant, winter*.—About 130 days at temperatures about 21° C.

*Root description*.—Medium in thickness, fibrous; typically brown in color, actual color of the roots is dependent on substrate composition, water quality, fertilizer type and formulation, substrate temperature and physiological age of roots.

*Rooting habit*.—Moderately freely branching; dense.

Plant description:

*Plant form and growth habit*.—Perennial evergreen shrub; uniform, upright and outwardly branching and low-mounding plant habit; vigorous growth habit; moderate growth rate.

*Branching habit*.—Freely branching habit; lateral branches potentially developing at every node; dense and bushy appearance; low requirement for pruning to maintain uniform plant habit.

*Plant height*.—About.

*Plant diameter, area of spread*.—About.

*Lateral branch description*.—Length, secondary branches: About. Diameter, secondary branches: About. Internode length: About. Strength: Strong. Aspect: About. Texture and luster: Color, young stems: Close to. Color, older stems: Close to.

*Leaf description*.—Arrangement: Alternate, single. Length: About. Width: About. Shape: Elliptic. Apex: Acute. Base: Cuneate to attenuate. Margin: Mostly entire, distally, crenate. Venation pattern: Pinnate. Texture and luster, upper surface: Smooth, glabrous; leathery; glossy. Texture and luster, lower surface: Smooth, glabrous; leathery; matte. Color: Developing leaves, upper surface: Developing leaves, lower surface: Fully expanded leaves, upper surface: Fully expanded leaves, lower surface.

*Petioles*.—Length: About. Diameter: About. Texture and luster, upper surface: Smooth, glabrous; leathery; somewhat glossy. Texture and luster, lower surface: Smooth, glabrous; leathery; matte. Color, upper surface: Close to. Color, lower surface: Close to.

Flower description: To date, flower development has not been observed on plants of the new *Cleyera*.

Garden performance: Plants of the new *Cleyera* have been observed have good garden performance and to tolerate rain, wind, full sunlight, shade and temperatures ranging from −11° C. to 38° C.

Pathogen & pest resistance: Plants of the new *Cleyera* have been observed not to be susceptible to infection from *Cercospora* spp., *Phylosticta* spp., and *Elsinoe leucospila*, and not to be susceptible to infestations from aphids, spider mites and red-headed flea beetles.

It is claimed:

1. A new and distinct cultivar of *Cleyera* plant named 'WMN-01' as illustrated and described.

* * * * *